United States Patent [19]

Coupek et al.

[11] 4,281,233
[45] Jul. 28, 1981

[54] HYDROPHILIC MACROPOROUS THREE DIMENSIONAL COPOLYMERS OF HYDROXYALKYL ACRYLATES OR METHACRYLATES WITH CROSSLINKING AGENTS AND THE METHOD OF THEIR MANUFACTURING

[75] Inventors: Jiři Coupek; Karel Filka; Jan Kocourek, all of Prague, Czechoslovakia

[73] Assignee: Ceskoslovenska akademie ved, Prague, Czechoslovakia

[21] Appl. No.: 170,767

[22] Filed: Jul. 21, 1980

Related U.S. Application Data

[62] Division of Ser. No. 900,892, Apr. 28, 1978.

[51] Int. Cl.$^3$ .............................. B01J 20/26; C08J 9/36
[52] U.S. Cl. ............................. 260/112 R; 210/198.2; 210/656; 260/17.4 SG; 521/149; 521/150
[58] Field of Search ........................... 210/656, 198 C; 260/17.4 SG; 521/147, 149, 84

[56] References Cited

U.S. PATENT DOCUMENTS

| | | | |
|---|---|---|---|
| 3,663,467 | 5/1972 | Albright | 521/149 |
| 3,925,267 | 9/1975 | Coupek et al. | 521/63 |
| 3,997,482 | 12/1976 | Tourkovec et al. | 521/149 |
| 4,035,316 | 7/1971 | Yen et al. | 521/149 |
| 4,079,021 | 3/1978 | Coupek et al. | 521/155 |

*Primary Examiner*—Morton Foelak

[57] ABSTRACT

The invention pertains to hydrophilic macroporous three dimensional copolymers of hydroxyalkyl methacrylates or hydroxyalkyl acrylates ($C_1$–$C_4$ hydroxyalkyl) with crosslinking monomers which contain covalently attached saccharides via an O-glycosidic bond. The invention further pertains to the method of manufacturing of these copolymers by the direct reaction of the basic three dimensional copolymer containing hydroxyl groups with saccharides or their derivatives in an inert organic solvent under catalysis of HCl, $BF_3$, or their mixtures at 20°–100° C. Saccharides and their derivatives are selected from the group comprising monosaccharides, oligosaccharides, deoxy sugars, amino saccharides, acylated saccharides, ether or halogen derivatives of monosaccharides and oligosaccharides, and the like. The invention also pertains to the application of these macroporous three dimensional copolymers with saccharides as sorbents and materials for the affinity chromatography for isolation of physiologically effective materials which contain free bonding sites for saccharides and are able to form specific complexes with saccharides.

1 Claim, No Drawings

HYDROPHILIC MACROPOROUS THREE DIMENSIONAL COPOLYMERS OF HYDROXYALKYL ACRYLATES OR METHACRYLATES WITH CROSSLINKING AGENTS AND THE METHOD OF THEIR MANUFACTURING

This is a division of Ser. No. 900,892, filed Apr. 28, 1978.

The invention pertains to hydrophilic macroporous three dimensional copolymers of hydroxyalkyl methacrylates or hydroxyalkyl acrylates with crosslinking comonomers containing covalently bound saccharides and to the method of their manufacturing by the direct reaction of the polymers with saccharides under catalysis of Lewis acids.

Hydrophilic macroporous copolymers of hydroxyalkyl methacrylates and hydroxyalkyl acrylates with alkylene dimethacrylates or alkylene diacrylates prepared by a suspension copolymerization of monomers in the presence of inert organic compounds in an aqueous or organic dispersion medium are known from the Czechoslovak Pat. No. 150,819, which corresponds to the British Pat. No. 1,370,477, and from the Czechoslovak Pat. No. 148,828, which corresponds to the British Pat. No. 1,331,087. Their outstanding mechanical properties, spherical shape of particles, and a macroporous structure, allowing to penetrate even considerably large molecules into the pores of carrier, led to the extensive applications of these materials in the gel, ion-exchange, adsorption, and affinity chromatography using water or aqueous solutions as an eluent. Utilizing of hydroxyalkyl methacrylate and hydroxyalkyl acrylate copolymers seems to be very perspective even in the hydrophobic chromatography which employs interactions between the lipophilic part of molecules which are separated and the relatively nonpolar matrix of carrier, the hydrophility of which is caused by the presence of nonionogenic hydroxyl groups in the side chains of copolymers.

However, this possible hydrophobic interaction between the carrier and molecules dissolved in water became undesirable for some applications. This holds everywhere the unambiguous interaction between the functional groups of carrier and an interacting compound is required (ion-exchange and affinity chromatography) or where the sorption interaction should be suppressed totally, as it is in the case of gel chromatography. The inner surface of macroporous copolymer has to be then hydrophilized by a chemical transformation of hydroxyl groups. The strongest hydrophilization may be attained by substitution of hydroxyl with ionogenic functional groups, e.g. by the methods according to the Czechoslovak Pat. Nos. 171,962 ,171,963 (U.S. Pat. No. 3,991,018) 177,507 or the British Pat. No. 1,500,532 and 1,499,134. However, also the presence of ionogenic functional groups is undesirable in numerous cases.

In some carriers designated for further chemical transformations, a low content of hydroxyl groups capable of transformation is disadvantageous because it causes a lower capacity of the final product than it was required. This comes true above all of the high mechanical stability of carrier is necessary (in microparticular sorbents for application in high-performance liquid chromatography) and, consequently, where the copolymers have to be prepared with a high content of a crosslinking agent, which does not contain hydroxyl groups. In these cases, the substitution of hydroxyl groups by the molecule of saccharide represents the solution of the required higher capacity for polymeranalogous transformations. In addition to this, the chemically bound saccharide represents, both in the basic form and the derivatized form, a basis for numerous polymeranalogous reactions where the glycosylated polymer is the reagent. Another advantage of the carrier containing chemically bound saccharides may be seen in the regenerability of carrier, because the original carrier which may be again modified is recovered by a hydrolytic cleavage under rather drastic conditions.

The most important carriers, among those which have been applied recently, are modified natural polysaccharides, glycoproteins linked to various carriers, and also sugars or their derivatives bound by a covalent bond to various matrices.

In the first group, the commercially available polysaccharides in a crosslinked form proved especially useful. Among them there are reckoned above all polydextrans crosslinked with epichlorohydrine, agarose gels, crosslinked gum arabic, chitin, etc. Glycoproteins occur mostly in a soluble form and require bonding to a natural or synthetic carrier for the purpose of affinity chromatography. The third group of sorbents includes monosaccharides or oligosaccharides bound most often to a polysaccharide carrier either directly or through a distance coupling (spacer) in the form of the reactive amino derivative. Another method employs the reactive functional groups of carrier or of the reactive interlink—divinylsulfone. Application of acrylamide carriers represents an important progress. They are prepared in three different ways: by modification of commercial preparations, by the synthesis of gels with active ester groups incorporated by polymerization and able to react with amino sugars, or by copolymerization of omega-unsaturated aliphatic glycosides with acrylamide.

The large number of various types of carriers gives evidence of the fact, that only few of them have nearly ideal properties. Modified natural polysaccharides are most easily available, however their choice is limited and they possess a low resistance against the attack of microorganisms. A disadvantage consists also in the fact, that some of these carriers cannot be prepared with a sufficient porosity while maintaining the satisfactory mechanical stability. The broader application of glycoproteins bound to a carrier is limited also by the complexity and high cost of preparation of affinity-chromatography materials as well as their low resistance to decomposition.

Many of the above disadvantages do not occur with acrylamide gels, which are substantially more resistant to the action of chemicals and microorganisms and allow the repeated use.

However, all above said materials are prepared in the form of soft, homogeneously crosslinked particles considerably swelling in aqueous solvents and changing their volume with the change of pH or ionic strength. They do not allow application of higher pressures and higher through-flow rates. From the standpoint of diffusion control of the kinetics of formation of affinity chromatography complexes and of their dissociation, these materials are not too much suitable.

An objective of this invention are hydrophilic macroporous three dimensional copolymers of hydroxyalkyl acrylates or hydroxyalkyl methacrylates, which contain 1-4 carbon atoms in the hydroxyalkyl group, with crosslinking agents selected from the group comprising divinyl or polyvinyl monomers, which copolymers are modified on the surface by saccharides or their derivatives linked by the covalent O-glycosidic bond and selected from the group comprising monosaccharides and oligosaccharides, deoxy sugars, amino sugars, acylated saccharides, and ether or halogen derivatives of monosaccharides and oligosaccharides.

Alkylene diacrylates, alkylene dimethacrylates, polyglycol diacrylates, polyglycol dimethacrylates, alkylene-bis-acrylamides, divinylbenzene, and others are advantageously used as crosslinking agents. Also other crosslinking agents may be employed including the copolymerizable compounds which contain two or more ethylenic double bonds to two or more nonconjugated vinyl groups of formula $CH_2=CH-$, as divinyltoluene, trivinylbenzene, divinylnaphthalene, divinylxylene, divinylethylbenzene, divinyl ether, divinyl ketone, allyl acrylate, and the like.

The crosslinking agent is added in the amount of at least 15 wt. %, advantageously in the amount of 30-50 wt. % in respect to monomeric mixture.

The polymerization of hydroxyalkyl acrylates or hydroxyalkylmethacrylates with crosslinking agents is carried out under the conditions of suspension radical polymerization in an aqueous medium in the presence of inert organic compounds, the character and concentration of which influence the distribution of pores of the obtained products, and in the presence of suspension stabilizers. Cyclohexanol, benzyl alcohol, cyclohexylamine, dodecyl alcohol, n-octyl alcohol, or their mixtures are advantageously used as the inert organic compounds. As the suspension stabilizers may serve, for example, polyvinylpyrrolidone, poly(vinyl alcohol), partially hydrolyzed poly(vinyl acetate), or some other natural polymeric materials (starch, pectins).

Spherical particles are formed in the suspension polymerization. The particles of the desirable distribution of size can be prepared by choosing the conditions of the reaction (the size, shape, and revolutions of the stirrer, concentrations of suspension stabilizer, and the like.

The method of manufacturing of the materials according to the invention represents the substitution of hydroxyl groups with saccharides under formation of the O-glycosidic bond, which is carried out in an inert organic solvent at temperature 20°-100° C. under catalysis of hydrogen chloride, boron trifluoride, or their mixtures.

The reaction of saccharides with macroporous copolymers proceeds very smoothly by mixing the suspension of a carrier in an organic inert solvent (advantageously dioxan or tetrahydrofuran) which contains the appropriate amount of hydrogen chloride, boron trifluoride, or their mixture. The solvents have to be dry and similarly is dried also HCl or $BF_3$ used for saturation. A finely ground saccharide is added into the suspension and the mixture is allowed to react under stirring or shaking at the ambient or elevated temperature 20°-100° C.). The presence of water in the reaction components reduces the yield of bonding reaction. Because the formation and hydrolysis of O-glycosidic bond represent an equilibrium reaction, the optimum operation conditions for bonding the maximum amount of saccharides were investigated. The increasing temperature up to 60°-70° C. increases the yield moderately. Further increase of temperature up to 100° C. led to the decrease of yield. The more expressive effect on the reaction yield has the concentration of catalyst (HCl or $BF_3$) which was followed up to 20 wt. %. The best results were achieved with the mixed catalyst $HCl+BF_3$ where hydrogen chloride acts apparently by a cocatalytic effect. On the other hand, the catalysis with $H_3PO_4$, $P_2O_5$, $H_2SO_4$, and other acids provide ineffective under the reaction conditions described.

Analysis of the content of bound saccharides was carried out by the method according Dubois after hydrolysis.

The materials prepared according to this invention combine the outstanding mechanical and hydrodynamic properties of the three dimensional hydroxyalkyl acrylate and methacrylate copolymers with a good hydrophility and suitable interaction properties comparable with polydextrans, agarose and cellulose materials, which find now the broadest application above all in biology and biochemistry.

The copolymers according to the invention have a high mechanical stability and pressure resistance, are relatively resistant towards both acid and alkaline hydrolysis, oxidation, and resistant to the effect of organic solvents. The copolymers swell in aqueous solutions only very little and the particles do not change their size with the changing ionic strength and pH.

The manufacturing method is not technologically demanding and provides reproducible yields in a broad range of reaction conditions.

The solvents, which are used for the reaction, have to dissolve hydrogen chloride and boron trifluoride well, without reacting with them at laboratory or moderately elevated temperatures. It is further desirable, that the solvents have the polar character which enables at least a partial dissolution of saccharides chosen for bonding to hydroxyalkyl acrylate or hydroxyalkyl methacrylate carriers. Dioxan or tetrahydrofuran are advantageously used.

The main advantage of the manufacturing method for glycosyl derivatives of hydroxyalkyl methacrylate and hydroxyalkyl acrylate copolymers consists in its simplicity and rapidness which highly exceeds all methods used until now for preparation of the similar type of sorbents. The mildness of preparation conditions for the materials according to the invention, the easily accessible reaction components, the resistance of matrix towards hydrolysis and microorganisms, simple handling and storage are further merits.

The modified carriers according to the invention represent basis for a new series of chromatographic materials with a high variety of uses above all for the separation of biopolymers and their fragments or for application in bonding of biologically active compounds designated for catalysis.

The copolymers according to the invention may be used, for example, as specific sorbents for isolation of physiologically effective compounds which contain free bonding sites and thus form with them specific complexes. Active compounds are selectively adsorbed from a mixture with inactive ballast. Admixtures on the copolymers according to this invention and are released from the formed complexes by exchange with the corresponding haptene or by elution with a suitable buffer solution.

The objective of the invention is further illustrated in examples, which however do not limit the scope of invention by any means.

EXAMPLE 1

A copolymer (5 g) of hydroxyethyl methacrylate with 39 wt. % of ethylene dimethacrylate, prepared by the suspension polymerization in an aqueous medium in the presence of inert solvent system consisting of cyclohexanol and lauryl alcohol (9:1) and having the exclusion limit of 300,000 daltons, was allowed to swell in 500 ml reaction flask in 70 ml of dioxan containing 17.5 wt. % of hydrogen chloride for 7 hours at laboratory temperature. Vacuum was then shortly applied to the mixture. Anhydrous finely powdered D-glucose (3 g) was added to the suspension which was then shaken for 14 hours at laboratory temperature. After that time, the reaction was stopped by pouring the reaction mixture into 1 liter of deionized water. The sugar derivative of gel was immediately separated by a sintered-glass filter and washed with deionized water to the neutral reaction and negative test on sugars. The glycosylated gel was eventually washed with ethanol, acetone and ether and dried at temperature 50° C. in vacuo to the constant weight. The content of bound sugar amounted to 13.5 wt. %.

EXAMPLE 2

Similarly as in Example 1, 4.2 g of the hydroxyethyl methacrylate copolymer was allowed to swell in 70 ml of dioxan saturated with gaseous hydrogen chloride to 5 wt. %. Then, 1.02 g of D-glucose was added and the suspension was shaken at temperature 45° C. for 10 hours; the suspension was poured into 1 liter of deionized water and further worked out as in Example 1. The content of bound sugar was 6.42 wt. %.

EXAMPLE 3

The copolymer (3.5 g) of 2-hydroxyethyl methacrylate with ethylene diacrylate of the molecular weight exclusion limit 300,000 daltons was allowed to swell for 12 hours in 60 ml of anhydrous dioxan which contained 6 wt. % of hydrogen chloride. N-Acetyl-D-glucosamine (1.3 g) was then added and the mixture was shaken at temperature 35° C. for 10 hours. The suspension was poured into 1 liter of deionized water and further worked out in the same way as in Example 1. The content of bound amino sugar was 8.15 wt. %.

EXAMPLE 4

The copolymer of 2-hydroxyethyl acrylate with ethylene dimethacrylate (5 g) of the exclusion limit 250,000 daltons was allowed to swell in 70 ml of dioxan, saturated with boron trifluoride to 7 wt. %, for 12 hours at laboratory temperature. Anhydrous D-glucose (3 g) was added to the reaction suspension and the reaction mixture was shaken for 8.5 hours at temperature 50° C. The reaction was stopped by pouring the mixture into 1 liter of deionized water and further worked out in the same way as in Example 1. The content of linked amino sugars was 12.4 wt. %.

EXAMPLE 5

The reaction was carried out analogously as in Example 1, with the distinction that the reaction temperature was increased to 70° C. at the hydrogen chloride concentration in dioxan 6%. The final content of covalently bound D-glucose was 6.25 wt. %.

EXAMPLE 6

The copolymer of 2-hydroxyethyl methacrylate with ethylene dimethacrylate (5 g) of the exclusion limit 300,000 daltons was mixed with 66 ml of dioxan and saturated with hydrogen chloride and boron trifluoride to the concentration 3.4 and 3.3 wt. %, respectively. The suspension was allowed to swell for 6.6 hours at the laboratory temperature with occasional shaking. Then, 3 g of anhydrous and finely ground D-glucose was added and the mixture was shaken at 35° C. for 1 hour. The reaction mixture was then kept for 12 hours at laboratory temperature under continuous shaking. The reaction was stopped by pouring the reaction mixture into 1 liter of deionized water and the polymer was further worked out in the same way as in Example 1. The content of bound sugar was 17.6 wt. %.

EXAMPLE 7

Bonding of disaccharide was carried out similarly as in Example 1, with the distinction that 3.26 g of finely ground maltose was used in the reaction and the reaction mixture was agitated on a laboratory shaker for 10 hours at temperature 40° C. The gel with bound disaccharide was worked out in the same way as in Example 1. The content of bound maltose was 9.7 wt. %.

EXAMPLE 8

The experiment was carried out in the same way as in Example 6, with the distinction that 6-O-methylglucose was used instead of D-glucose. The final content of the bound ether derivative of glucose was 15.2 wt. %.

EXAMPLE 9

The bound halogen derivative of saccharide was prepared as in Example 6, with the distinction that 3 g of 6-fluoroglucose was used for the reaction. The resulting product was worked out in the same way as in Example 6 and the content of bound 6- fluoroglucose was 14.78 wt. %.

EXAMPLE 10

The lyophilized active fraction of proteins from soya beans (*Glycine soja*) (400 mg) was dissolved in 4 ml of water. The undissolved residues were removed by centrifugation and sodium chloride was added to the supernatant up to concentration 0.9%. The solution of 4 ml of the active protein fraction (the determined activity of 1% solution against the tryptinised blood cells of group $A_1$ was 64) was applied to the column of poly(2-hydroxyethyl methacrylate-co-ethylene dimethacrylate) (mol. wt. exclusion limit 300,000 daltons) with 7.66 wt. % of bound D-galactose (weight of the dry carrier 4 g), which was equilibrated with physiologic saline. After soaking of the sample, the column was eluted with saline at the flow rate 8 ml/h and 4 ml fractions were collected. The eluate in fractions 3–5 was active in haemaglutination. From the fraction 20, the elution started with the 0.2 M solution of D-galactose in saline. The fractions 22–24 were combined, dialysed for 48 hours against 4×2 liters water and lyophilised. The yield was 6.2 mg; activity of 1% solution 4096.

EXAMPLE 11

The solution containing 200 mg of active proteins from lentils (*Lens esculenta*) (activity of 1% solution 64) in 2 ml of physiologic saline was applied to the column (1×30 cm) containing poly(2-hydroxyethyl methacrylate-co-ethylene dimethacrylate) (mol. wt. exclusion limit 300,000 daltons) with 8.25 wt. % of covalently bound D-glucose which was equilibrated with saline. After soaking of the sample, the column was eluted with saline at the flow rate 8 ml/h and 4 ml fractions were collected. The eluate in fractions 3-5 was active in haemaglutination. The elution with 0.2 M solution of D-glucose in saline was started from the 25th fraction. The fractions 28-30 were combined, dialysed for 48 hours against 4×2 l of water, and lyophilised. The yield was 5.8 mg; activity of 1% solution 256.

EXAMPLE 12

The solution of 250 mg of the active fraction of proteins from lentils (*Lens esculenta*) (activity of 1% solution 64) in 2.5 ml of physiologic saline was applied to the column (1×30 cm) containing 4 g of poly(2-hydroxyethyl acrylate-co-ethylene diacrylate) (mol. wt. exclusion limit 500,000 daltons) with 9.0% of covalently bound mannose, which was equilibrated with saline. After soaking of the sample, the column was eluted with saline at the flow rate 8 ml/h and 4 ml fractions were collected. The eluate in fractions 3-5 was active in haemaglutination. The elution with 0.2 M solution of D-mannose in saline was started from the 28th fraction. The fractions 31-35 were combined, dialysed for 48 hours against 4×3 l of water and lyophilised. The yield was about 1 mg.

EXAMPLE 13

The solution of 300 mg of the lyophilised extract from seeds of *Ricinus sommunis L.* (activity of 1% solution 8192) in 3 ml of physiologic saline was applied to the column (1×30 cm) packed with 4 g of spherical macroporous poly(2-hydroxyethyl methacrylate -co- ethylene dimethacrylate) (mol. wt. exclusion limit 1,000,000 daltons) with 7.66 wt. % of chemically bound D-galactose, which was equilibrated with saline. After soaking of the sample, the column was eluted with saline at the flow rate 8 ml/h and 4 ml fractions were collected. The elute in the 3rd fraction was active in haemaglutination. The elution with 0.2 M solution of D-galactose in saline was started from the 21st fraction. The fractions 24-28 were combined, dialysed for 48 hours against 4×3 l of water, and lyophilised. The yield was 77.2 mg; activity of 1% solution was 32,768.

EXAMPLE 14

The solution containing 700 mg of the haemaglutination active fraction of proteins from seeds of *Ulex edropaeus L.* in 6 ml of 0.15 phosphate buffer solution of pH 7.9 was applied to the column (1×30 cm) containing 4 g of spherical macroporous poly(2-hydroxyethyl methacrylate -co- ethylene dimethacrylate) (mol. wt. exclusion limit 300,000 daltons) with 5.42 wt. % of bound L-fucose, which was equilibrated with the same buffer solution. After soaking of the sample, the column was eluted with the same buffer solution at the flow rate 15 ml/h and 5 ml fractions were collected. The elution with 50 ml of 0.2 M solution of L-fucose in the above buffer solution was started from the 40th fraction and, after soaking of the L-fucose solution, it was continued with the phosphate buffer solution at the unchanged flow rate. The fractions 43-48 were combined dialysed for 48 hours against 4×5 l of water, and lyophilised. The yield was 7.1 mg.

EXAMPLE 15

The haemaglutination active extract (5 ml) obtained from 1.5 g of albumine glands of snail (*Helix pomatia*) was applied to the column (1×20 cm) containing 3.1 g of spherical macroporous poly(2-hydroxyethyl methacrylate -co- ethylene dimethacrylate) with 8.15 wt. % of covalently bound N-acetyl-D-glucosamine, which was equilibrated with physiologic saline. After soaking of the sample, the column was eluted with saline at the flow rate 8 ml/h and 4 ml fractions were collected. The eluate of no fraction was haematoglutination active. The elution with 0.2 M solution of N-acetyl-D-glucosamine in saline was started from the 23rd fraction and with the glycine buffer solution of pH 2.7 from the 38th fraction. The fractions 26-29 were collected, dialysed for 48 hours against 4×3 l of water and lyophilized. The yield was 16.3 mg; activity of 1% solution 32,768.

EXAMPLE 16

The haemaglutination active extract (20 ml) from Jack beans meal (activity of 1% solution against trypsinised blood cells was 512) was applied to the column (1×30 cm) containing 4 g of macroporous poly(2-hydroxyethyl methacrylate -co- ethylene dimethacrylate) with 8% of bound D-glucose, which was equilibrated with physiologic saline. After soaking of the sample, the column was eluted with saline at the flow rate 8 ml/h and 4 ml fractions were collected. The eluate in fractions 3-6 was active in haemaglutination. The elution with 0.2 M solution of D-glucose in saline was started from the 21st fraction. The fractions 23-27 were combined, dialysed for 48 hours against 4×3 l of water, and lyophilised. The yield was 41.1 mg; activity of solution 2048.

EXAMPLE 17

The sample (2 ml) containing 50 mg of Concanavaline A isolated from Jack beans meal (activity of 1% solution 512) was applied to the column (1×30 cm) containing 4 g of macroporous poly(2-hydroxyethyl methacrylate -co- ethylene dimethacrylate) with 8.25 wt. % of bound D-glucose, which was equilibrated with saline. After soaking of the sample, the column was eluted with saline at the flow rate of 8 ml/h and 4 ml fractions were collected. No fraction contained the eluate with haemaglutination activity. The elution with 0.2 M solution of D-glucose in saline was started from the 17th fraction and with the glycine buffer solution of pH 2.7 from the 28th fraction. The fractions 19-22 were combined, dialysed for 48 hours against 4×3 l of water, and lyophilised. The yield was 46.9 mg; activity of 1% solution against trypsinised blood cells was slightly higher than 512.

EXAMPLE 18

The copolymer of hydroxyethyl methacrylate with ethylene dimethacrylate (4.2 g, mol. wt. exclusion limit 300,000 daltons) was allowed to swell in 70 ml of 6 wt. % HCl solution in dioxan for 12 hours. N-Acetyl-D-galactosamine (1.046 g) was then added and the suspension was shaken for 6 hours at laboratory temperature and subsequently for 6 hours at 40° C. The reaction mixture was poured into 1 liter of deionized water, and washed to neutral reaction and negative reaction on sugars. The copolymer was then washed with ethanol, acetone, and ether and dried in vacuo at 50° C. to the constant weight. The column 1×30 cm containing 4 g of the above described derivative with bound N-acetyl-D-galactosamine was equilibrated in physiologic saline. The solution of 228.6 mg of the haemaglutination active protein fraction from seeds of *Dolichos biflorus L.* in 3 ml of saline was applied on the column. After soaking of the sample, the column was eluted with saline at the flow rate 10 ml/h and 5 ml fractions were collected. When 155 ml of effluent was collected, the affinity bound protein was eluted with 0.2 M N-acetyl-D-galactosamine (5 ml) and then the elution with saline was continued. Individual fractions were measured in a UV spectrophotometer at the wave length 280 nm. The fractions containing proteins were combined (total volume 15 ml), dialysed against 4×2 l of water, and lyophilised. The yield was 17.4 mg; activity of the final product against the blood group $A_1$ was 4095, while that of the original sample was 128.

EXAMPLE 19

The solution containing 562.7 mg of lyophilised extract from seeds of *Ricinus communis* in 6 ml of saline was applied to the column (1×30 cm) containing 4 g of macroporous poly(2-hydroxyethyl acrylate -co- ethylene diacrylate) with 14.16% of bound D-galactose, which was equilibrated with physiologic saline. After soaking of the sample, the column was eluted with saline at the flow rate 8 ml/h and 4 ml fractions were collected. The eluate in fractions 3–8 was active in haemaglutination. Also the absorbance measured at 280 nm was maximum in these fractions. After elution of the column with 200 ml of saline, the carrier was eluted with 0.2 M D-galactose in saline. The fractions containing protein were combined (the total was 40 ml), dialysed against 4×4 l of water for 48 hours, and the product was lyophilised. The yield was 159.8 mg. Activities of 1% solutions against the blood cells of group $A_1$ Sulfate fraction before isolation: 4096

Pure protein after isolation: 16,384. The purity of preparation was checked by an alkaline discontinuous electrophoresis on polyacrylamide gel.

EXAMPLE 20

The protein fraction (300 mg) from seeds of *Ricinus communis* was dissolved in 20 ml of physiologic saline. The solution was titrated against the blood cells of group $A_1$; activity in the 12th test-tube was 4096. Then, 4 g of the same copolymer with bound D-galactose as in Example 19 was added. The decrease of activity with time was followed. The activity settled after 8 hours. The adsorbent was removed by filtration and washed with saline. Its whole amount was filled into a column, eluted with saline to the disappearance of activity and decrease of adsorbance to the original value of saline. The bound protein was then eluted with 0.2 M solution of D-galactose in physiologic saline. The fractions containing proteins were combined, dialysed against 4×4 l of deionised water for 48 hours, and lyophilised. The yield 238.4 mg corresponds to the capacity of 59.6 mg per 1 g of the dry copolymer with bound D-galactose.

EXAMPLE 21

The isolation was carried out analogously as in Example 20, with the distinction that the original amount of protein was 184.4 mg in 20 ml of physiologic saline and 3.05 g of the copolymer containing 13.08 wt. % of D-glucose was used as adsorbent. The yield of pure protein 149.6 mg corresponds to the capacity of 49.4 mg/g of dry adsorbent.

We claim:

1. An affinity chromatography process for the isolation of physiologically effective materials from active protein comprises:
    (a) applying a physiologic saline solution of said protein to a column of hydrophilic macroporous three dimensional copolymer of a hydroxyalkyl acrylate or a hydroxyalkyl methacrylate, said hydroxyalkyl containing 1 to 4 carbon atoms, and containing a crosslinking agent in the amount of 15 to 50 weight percent selected from the group consisting of ethylene diacrylate and ethylene dimethacrylate, wherein said copolymer contains, after glycosylation reaction at the surface, saccharides or their derivatives, selected from the group consisting of monosaccharides, oligosaccharides, deoxy sugars, amino sugars, acylated saccharides, either or halogen derivatives of monosaccharides and oligosaccharides, equilibrated with physiologic saline solution;
    (b) eluting said column with physiologic saline solution; and
    (c) recovering fractions active in haemaglutination.

* * * * *

UNITED STATES PATENT AND TRADEMARK OFFICE
CERTIFICATE OF CORRECTION

PATENT NO. : 4,281,233
DATED : July 28, 1981
INVENTOR(S) : Jiri COUPEK ET AL

It is certified that error appears in the above-identified patent and that said Letters Patent are hereby corrected as shown below:

On the cover sheet should be inserted --

[30]    FOREIGN APPLICATION PRIORITY DATA

May 3, 1977 [CS]  Czechoslovakia  2890/77

May 3, 1977 [CS]  Czechoslovakia  2891/77           --

Signed and Sealed this

Ninth Day of February 1982

[SEAL]

Attest:

GERALD J. MOSSINGHOFF

Attesting Officer    Commissioner of Patents and Trademarks